(12) United States Patent
Beebe et al.

(10) Patent No.: US 10,519,412 B2
(45) Date of Patent: Dec. 31, 2019

(54) STAMP AND METHOD OF TRANSFERRING PARTICLES TO CELLS OF A CELL CULTURE

(71) Applicant: Wisconsin Alumni Research Foundation, Madison, WI (US)

(72) Inventors: David Beebe, Monona, WI (US); Erwin Berthier, Madison, WI (US); Mary Regier, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 493 days.

(21) Appl. No.: 14/744,765

(22) Filed: Jun. 19, 2015

(65) Prior Publication Data

US 2016/0369220 A1    Dec. 22, 2016

(51) Int. Cl.
*C12M 1/00*   (2006.01)

(52) U.S. Cl.
CPC .................................. *C12M 29/00* (2013.01)

(58) Field of Classification Search
None
See application file for complete search history.

(56) References Cited

U.S. PATENT DOCUMENTS

| 8,835,187 B2 | 9/2014 | Love et al. | |
| 2009/0191355 A1* | 7/2009 | Lee | B82Y 10/00 |
| | | | 427/535 |
| 2010/0025243 A1* | 2/2010 | Beebe | B01L 3/5027 |
| | | | 204/455 |

OTHER PUBLICATIONS

Han et al., "Polyfunctional response by human T cells result from sequential release of cytokines", PNAS, Jan. 31, 2012, vol. 109, No. 5, pp. 1607-1612.
Sip et al., "Microfluidic transwell inserts for generation of tissue culture-friendly gradients in well plates", Lab Chip, 2014, 14, 302-314.
http://www.cellbiolabs.com, Nov. 18, 2015.

* cited by examiner

*Primary Examiner* — Renee Claytor
*Assistant Examiner* — Evelyn Y Pyla
(74) *Attorney, Agent, or Firm* — Boyle Fredrickson, S.C.

(57) ABSTRACT

A stamp and a method for transferring particles to cells of a cell culture. The stamp includes a body having upper and lower surfaces. The lower surface includes a recessed portion. A gel extends along the recessed portion of the lower surface of the body and including the particles patterned therein. The body is configured to move between a first position wherein the gel is isolated from the cells of the cell culture and a second position wherein the particles patterned in the gel communicate with the cells of the cell culture through diffusion.

15 Claims, 7 Drawing Sheets

STAMP AND METHOD OF TRANSFERRING PARTICLES TO CELLS OF A CELL CULTURE

REFERENCE TO GOVERNMENT GRANT

This invention was made with government support under EB010039 awarded by the National Institutes of Health. The government has certain rights in the invention.

FIELD OF THE INVENTION

This invention relates generally to the study of cells, and in particular, to a device and method for transferring particles to cells of a cell culture to facilitate the broad-spectrum analysis of cells and cell associated factors with two-dimensional (2D) spatial resolution and minimal fluid handling or processing.

BACKGROUND AND SUMMARY OF THE INVENTION

Cells are constantly receiving, integrating, and reacting to physical and molecular signals. These signals define the cellular microenvironment, which varies from location to location within in vivo systems and in vitro cultures. Spatiotemporial patterns of soluble factors influence cellular behaviors such as growth, migration, and differentiation. Mimicking these chemical and molecular patterns in vitro is of particular interest for those seeking to understand cellular regulation in vitro and in vivo. Current technologies allowing patterning of soluble factors in gradients and other concentration profiles are limited to microfluidic devices or culture in or under a hydrogel. However many standard cell culture procedures and protocols calling for patterning of surface associated factors require open systems.

In addition to heterogeneity in their microenvironments, within a population, cells exhibit individual-to-individual heterogeneity. As a result, measures of behaviors averaged over the population may not accurately reflect the state of a specific cell within that population. The differences have led to the emergence of single cell analysis tools. However, current procedures and readouts for these analyses are not ideal, as they either fail to provide the user historical information about a cells origin in terms of microenvironment or they limit throughput and analyte detection. For example, in flow cytometry, the expression of proteins may be measured on a cell-by-cell basis. But, any information regarding the location of where the cells where first removed from their microenvironment and any information about the cell's position within a culture are lost, thereby leaving analyses ignorant of the effects of diverse microenvironments on diverse cell populations.

Conversely to methods requiring the removal of cells from their microenvironment, image based analysis can be used to track cellular histories. These methods are limited in throughput, requiring continuous monitoring of a limited number of locations in cultures, and the microscope's filters and light source dictate the number of analytes that can be imaged. Thus, important measures often cannot be obtained simultaneously and those that can be obtained are evaluated using image analyses methods that are relatively computationally intensive.

Therefore, it is a primary object and feature of the present invention to provide a stamp and a method for transferring particles to cells of a cell culture.

It is a further object and feature of the present invention to provide a stamp and a method for transferring particles to cells of a cell culture that enables direct correlation between differences within a heterogeneous cell population and the position of given cells within a microenvironment.

It is a still further object and feature of the present invention to provide a stamp and a method for transferring particles to cells of a cell culture that is simple to use and inexpensive to manufacture.

In accordance with the present invention, a stamp is provided for transferring particles to cells of a cell culture. The stamp includes a body having upper and lower surfaces. The lower surface includes a recessed portion. A gel extends along the recessed portion of the lower surface of the body and includes the particles pre-patterned therein. The body is configured to move between a first position wherein the gel is isolated from the cells of the cell culture and a second position wherein the particles pre-patterned in the gel communicate with the cells of the cell culture.

The body includes first and second passages extending between the upper surface and the recessed portion of lower surface thereof. The gel is received in the first and second passages through the body. The gel in the first passage defines a first well. The first well is adapted for receiving a first solution therein. The gel in the second passage defines a second well. The second well is adapted for receiving a second solution therein. At least one of the first and second solutions includes the particles to be transferred.

In accordance with a further aspect of the present invention, a method of transmitting particles to cells of a cell culture is provided. The particles are patterned in a gel extending along a portion of a lower surface of a stamp. The stamp is positioned such that the particles in the gel extending along the lower surface of the stamp communicate with the cells of the cell culture. The particles in the gel are allowed to diffuse into the cells of the cell culture.

The stamp includes a body has an upper surface, a lower surface having a recessed portion, and first and second passages extending between the upper surface and the recessed portion of lower surface thereof. The gel extends along the recessed portion of the lower surface of the body. The body may also include first and second passages extending between the upper surface and the recessed portion of lower surface thereof. The gel is received in the first and second passages through the body. The gel in the first passage defines a first well. The first well is adapted for receiving a first solution therein. The gel in the second passage defines a second well. The second well is adapted for receiving a second solution therein.

The step of patterning the particles includes the additional step of depositing a first solution in the first well. The first solution includes the particles. Thereafter, the particles are allowed to diffuse into the gel. The particles in the gel form a gradient between the first and second passages in the body along the recessed portion of the lower surface. It is contemplated to deposit cell culture media on the cell culture prior to the step of positioning the stamp.

In accordance with a still further aspect of the present invention, a method of transmitting particles to cells of a cell culture is provided. The method includes the steps of forming a cell culture on a base and patterning the particles in a gel extending along a lower surface of a stamp. Cell culture media is deposited on the cell culture and the stamp is positioned in communication with the cell culture media such that the particles in gel extending along the lower surface of the stamp communicate with the cells of the cell culture. The particles in the gel are allowed to diffuse into the cells of the cell culture through the cell culture media.

The stamp includes a body has an upper surface, a lower surface having a recessed portion, and first and second passages extending between the upper surface and the recessed portion of lower surface thereof. The gel extends along the recessed portion of the lower surface of the body. The body also includes first and second passages extending between the upper surface and the recessed portion of lower surface thereof. The gel is also received in the first and second passages through the body. The gel in the first passage define a first well. The first well is adapted for receiving a first solution therein. The gel in the second passage defines a second well. The second well is adapted for receiving a second solution therein.

The step of patterning the particles includes the additional step of depositing a first solution in the first well. The first solution include the particles. The particles are allowed to diffuse into the gel and form a gradient between the first and second passages in the body along the recessed portion of the lower surface. The particles are first particles and the method may include the additional step of depositing a second solution in the second well. The second solution includes second particles. The second particles are allowed to diffuse into the gel. The second particles in the gel form a second gradient from the between the second well and the first well in the body along the recessed portion of the lower surface.

BRIEF DESCRIPTION OF THE DRAWINGS

The drawings furnished herewith illustrate a preferred construction of the present invention in which the above advantages and features are clearly disclosed as well as other which will be readily understood from the following description of the illustrated embodiment.
In the drawings.

DETAILED DESCRIPTION OF THE DRAWINGS

Figure 1:
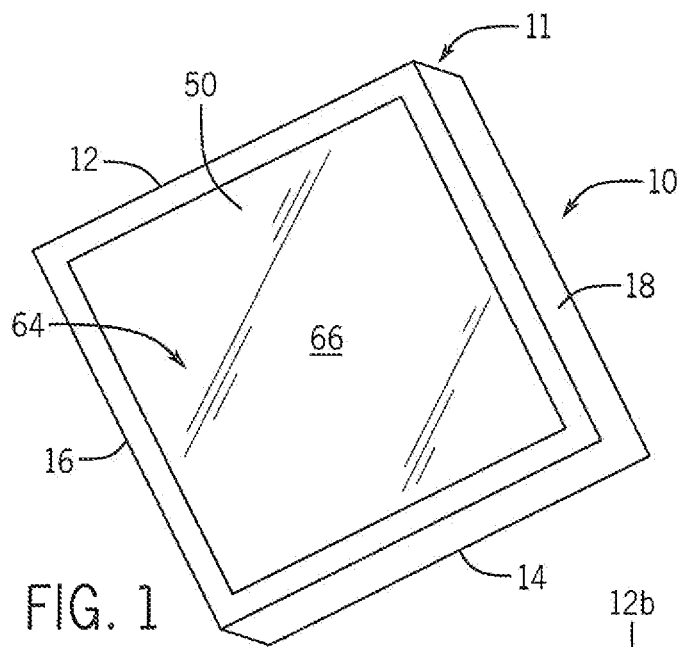
FIG. 1 is an isometric view of a stamp in accordance with the present invention.
Figure 2:
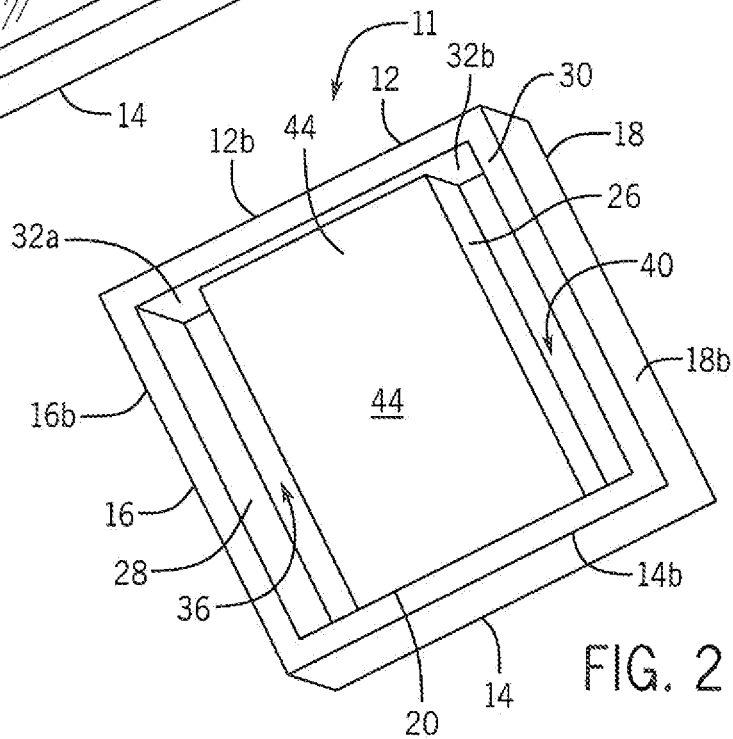
FIG. 2 is an isometric view of a base for the stamp of FIG. 1.
Figure 3:
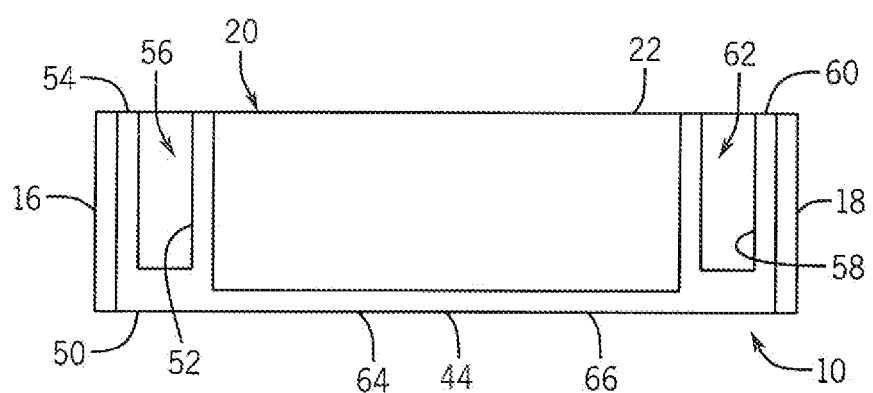
FIG. 3 is a cross sectional view of the stamp of the present invention.

Referring to FIGS. 1-5, a stamp for use in the methodology of the present invention is generally designated by the reference numeral 10. In the depicted embodiment, stamp includes base 11 having a generally square configuration, FIG. 2. Base 11 is defined by first and second sidewalls 12 and 14, respectively, and first and second end walls 16 and 18, respectively. Upper edges 12*a* and 14*a* of first and second side walls 12 and 14, respectively, and upper edges 16*a* and 18*a* of first and second end walls 16 and 18, respectively, are generally co-planer, FIG. 4. Similarly, lower edges 12*b* and 14*b* of first and second sidewalls 12 and 14, respectively, and upper edges 16*ba* and 18*b* of first and second end walls 16 and 18, respectively, are generally co-planer.

Base 11 includes central portion 20 having an upper surface 22 which extends between upper edges 12*a* and 14*a* of first and second side walls 12 and 14, respectively. Upper surface 22 of central portion 20 is generally co-planar with upper edges 12*a* and 14*a* of first and second side walls 12 and 14, respectively, and with upper edges 16*a* and 16*b* of first and second end walls 16 and 18, respectively. Central portion 20 is further defined by first and second sides 24 and 26, respectively. First and second sides 24 and 26, respectively, of central portion 20 are generally parallel to each other.

Figure 4:
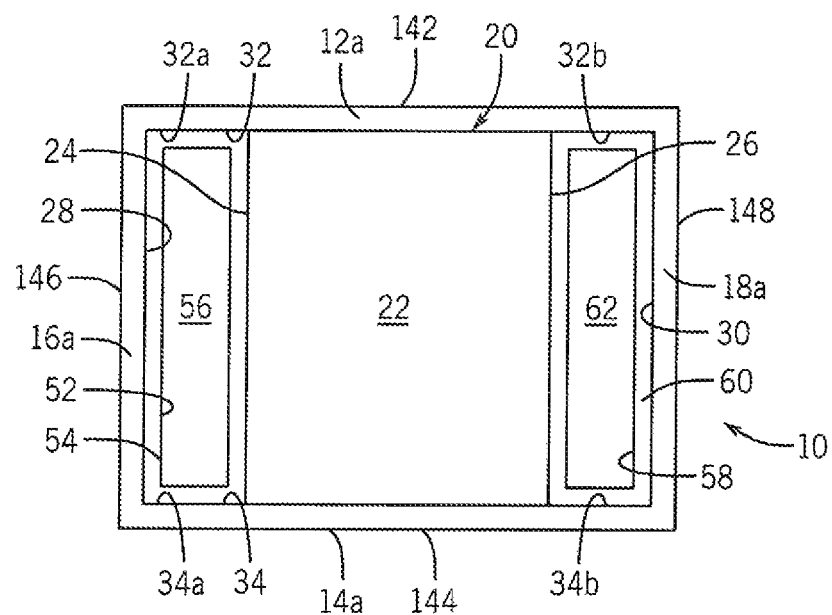
FIG. 4 is a top plan view of the stamp of FIG. 3.

As best seen in FIG. 4, first side 24 of central portion 20 is generally co-planar with and directed towards inner surface 28 of fast end wall 16. First side 24 of central portion 20, inner surface 28 of first end wall 16 and first portions 32*a* and 34*a* of inner surfaces 32 and 34, respectively, of first and second side walls 12 and 14, respectively, define first gel cavity 36 extending through base 11. In the depicted embodiment, first gel cavity 36 has a generally rectangular cross section. However, other configurations of first gel cavity 36 are possible without deviating from the scope of the present invention.

Second side 26 of central portion 20 is generally co-planar with and directed towards inner surface 30 of second end wall 18. Second side 26 of central portion 20, inner surface 38 of second end wall 18 and second portions 32*b* and 34*b* of inner surfaces 32 and 34, respectively, of first and second side walls 12 and 14, respectively, define second gel cavity 40 extending through base 11. In the depicted embodiment, second gel cavity 40 has a generally rectangular cross section. However, other configurations of second gel cavity 40 are possible without deviating from the scope of the present invention.

Lower surface 42 of central portion 20 extends between inner surfaces 32 and 34 of first and second side walls 12 and 14, respectively. Lower surface 42 of central portion 20 is generally planar and recessed from a plane co-planar with lower edges 12*b* and 14*b* of first and second side walls 12 and 14, respectively, and lower edges 16*b* and 18*b* of first and second end walls 16 and 18, respectively. Lower surface 42 and the plane co-planer with lower edges 12*b* and 14*b* of first and second side walls 12 and 14, respectively, and lower edges 16*b* and 18*b* of first and second end walls 16 and 18, respectively, define a gradient cavity 44 therebetween. Gradient cavity 44 communicates with first and second gel cavities 36 and 40, respectively, as hereinafter described.

Gel 50 is provided in first and second gel cavities 36 and 40, respectively, and in gradient cavity 44 along lower surface 42 of central portion 20 of base 11. It is contemplated for gel 50 to take the form of an agarose gel. As is known, agarose gel has a high degree of physical, chemical and thermal stability and exhibits limited interaction with biomolecules. It is noted, however, the gel 50 may take other forms without deviating from the scope of the present invention. First portion 52 of gel 50 in first gel cavity 36 includes upper surface 54 which is generally co-planar with upper surface 22 of central portion 20. First well 56 is formed in upper surface 54 of first portion 52 of gel 50 for reasons hereinafter described. In the depicted embodiment, first well 56 has a generally rectangular cross section. However, other configurations of first well 56 are possible without deviating from the scope of the present invention. Second portion 58 of gel 50 in second gel cavity 40 includes upper surface 60 which is generally co-planar with upper surface 22 of central portion 20. Second well 62 is formed in upper surface 56 of second portion 58 of gel 50, for reasons hereinafter described. In the depicted embodiment, second well 62 has a generally rectangular cross section. However, other configurations of second well 62 are possible without deviating from the scope of the present invention. Third portion 64 of gel 50 in gradient cavity 44 has a lower surface 66 which is generally co-planar with lower edges 12b and 14b of first and second side walls 12 and 14, respectively, and lower edges 16b and 18b of first and second end walls 16 and 18, respectively.

In operation, second well 62 in second portion 58 of gel 50 is filled with a first predetermined solution, such as deionized water. A predetermined fluid having a known concentration of particles 68, such as cells, molecules, chemical species, organisms or the like, therein are introduced or loaded into first well 56 in first portion 52 of gel 50. Molecules may include those that influence cell behaviors, such as chemokines that induce chemotactic migration, morphogens that influence differentiation and development, or growth factors that stimulate proliferation. Chemical species such as cell function inhibitors/activators or nutrients may also be patterned. Alternatively, cell-sourced molecules may be patterned by culturing mammalian or microbial cells in one or more gel cavities. Thereafter, the predetermined fluid diffuses through first portion 52 of gel 50 into third portion 64 of gel 50 in gradient cavity 44 so as to create a concentration gradient of particles in third portion 64 of gel 50 in gradient cavity 44 from first well 56 to second well 62 over a predetermined time period.

Figure 5:
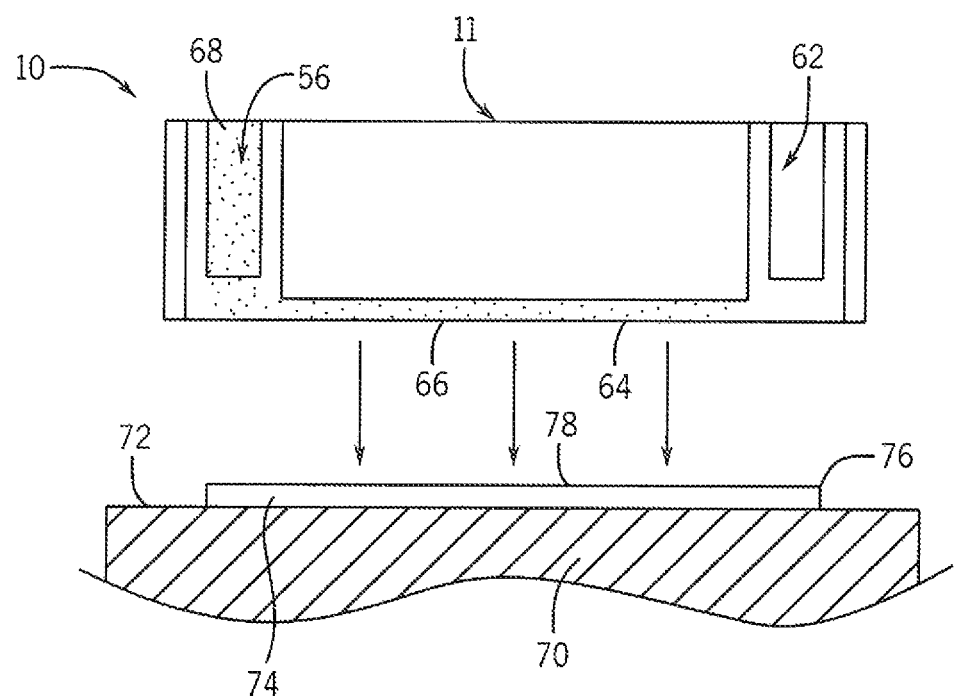
FIG. 5 is a cross-sectional view of the stamp of FIG. 3 prior to engagement with a cell culture.
Figure 6:
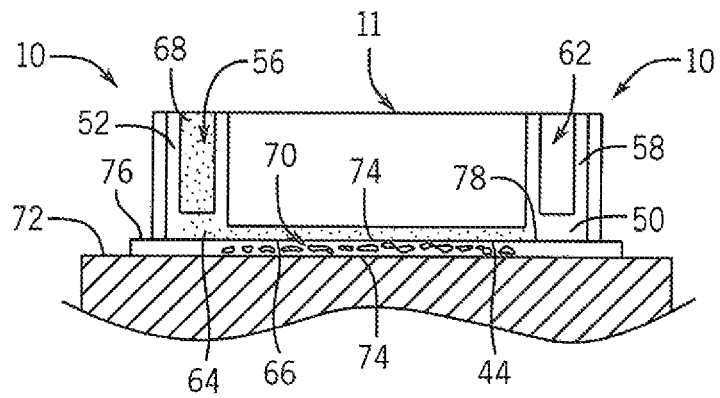
FIG. 6 is a cross-sectional view of the stamp of FIG. 3 showing engagement of the device with the cell culture.
Figure 7:
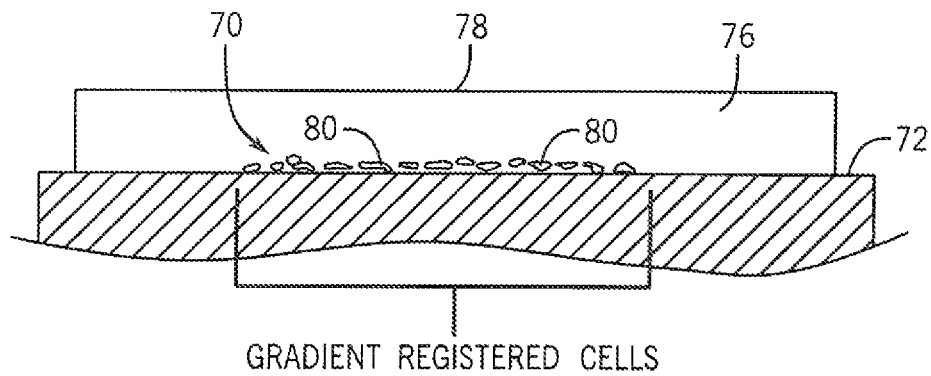
FIG. 7 is a cross-sectional view show the cell culture after engagement with the stamp of the present invention.

During or after the gradient has formed in gradient cavity 44, stamp 10 is positioned over a cell culture, generally designated by the reference numeral 70, which has been provided on cell culture surface 72, FIG. 5. Cell culture 70 includes a plurality of cells 74 received within cell culture media 76. Stamp 10 is positioned such that lower surface 66 of third portion 64 of gel 50 in gradient cavity 44 communicates with upper surface 78 of cell culture media 76, FIG. 6. Stamp 10 in maintained in positioned a desired incubation period. During the incubation period, particles 68 in gel 50 diffuse from lower surface 66, through cell culture media 76 and into the plurality of cells 74 to provide for gradient registered cells 80. At the conclusion of the incubation period, stamp 10 is removed and gradient registered cells 80 are processed according to a desired application, FIG. 7. For example, cell identification and location mapping by microscopy, analysis of single cells and subpopulations can be performed by techniques such as single cell PCR, flow cytometry, or PCR of sorted subpopulations. Registry signals may be used to relate gene expression or some other cellular characterization metric back to a position within the original microenvironment.

It can be appreciated that the methodology heretofore described will enable direct correlation between differences within a heterogeneous cell population and the position of given cells within a microenvironment. As such, deep characterizations of cellular heterogeneity/microenvironment relationships, along with the potential to reveal previously undiscovered or understudied aspects of cellular interactions and regulation, may be enabled.

Figure 8:
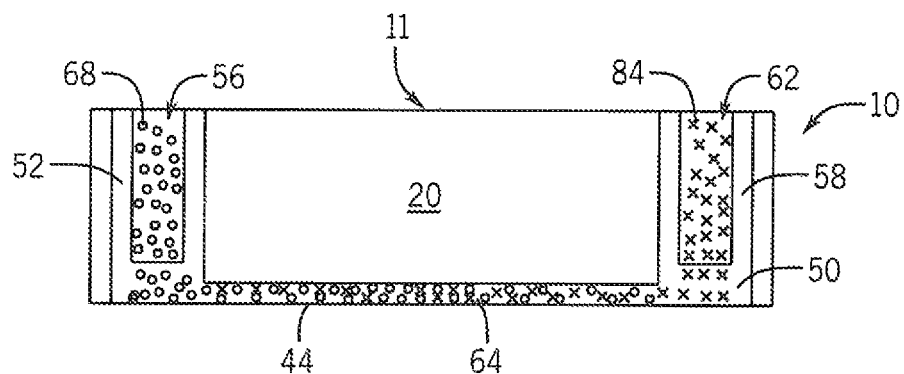
FIG. 8 is an enlarged, cross-sectional view of the stamp of the present invention having multiple gradients formed therein.

In addition to creating the concentration gradient of particles in third portion 64 of gel 50 in gradient cavity 44 from first well 56 to second well 62, it is contemplated to create a second concentration gradient of particles in third portion 64 of gel 50 in gradient cavity 44 from second well 62 to first well 56, FIG. 8. More specifically, second well 62 in second portion 58 of gel 50 may be filled with a second predetermined fluid having a known concentration of second particles 84, different from particles 68, such as cells, molecules, chemical species, organisms or the like. Thereafter, the second predetermined fluid diffuses through second portion 58 of gel 50 into third portion 64 of gel 50 in gradient cavity 44 so as to create a concentration gradient of particles 84 in third portion 64 of gel 50 in gradient cavity 44 from second well 62 to first well 56 over a predetermined time period.

Figure 9A:
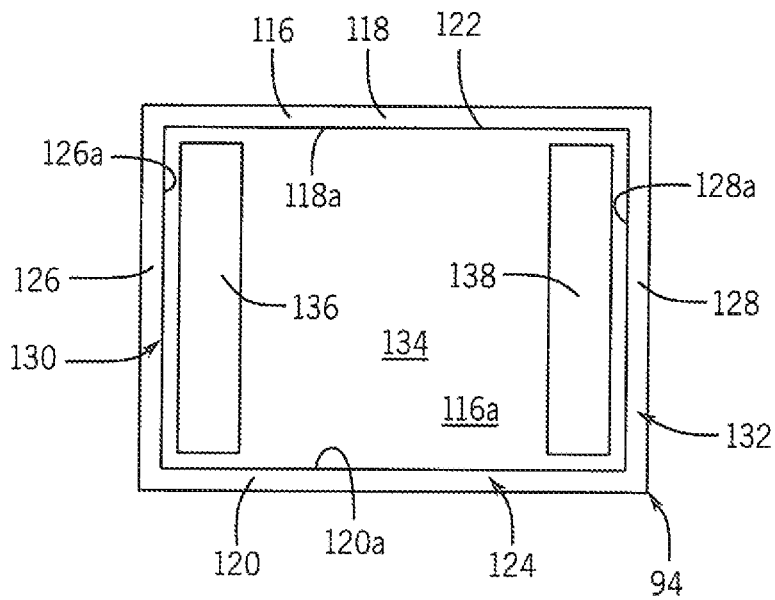
FIG. 9*a* is a bottom plan view of an upper portion of a mold used to fabricate a stamp in accordance with the present invention.
Figure 9B:
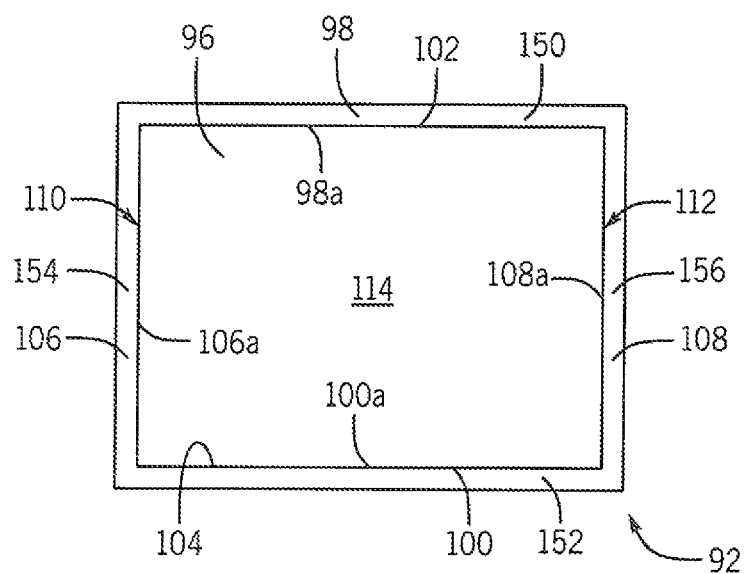
FIG. 9*b* is a top plan view of a bottom portion of the mold used to fabricate the stamp of the present invention.
Figure 10:
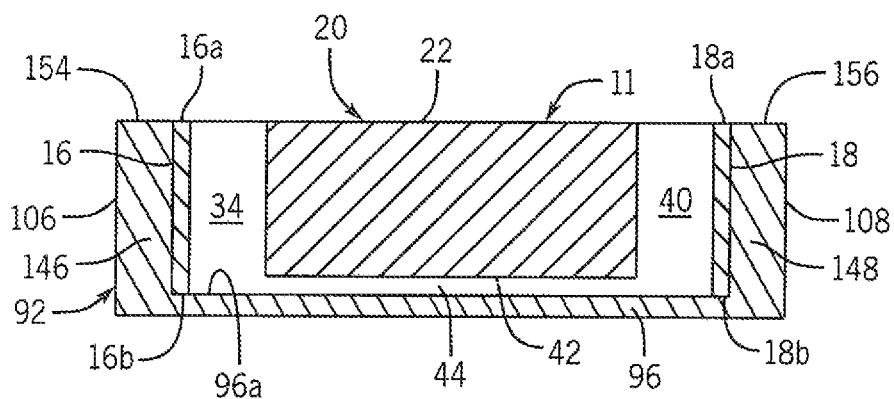
FIG. 10 is a cross-sectional view of the bottom portion of the mold receiving the base of the stamp of the present invention.
Figure 11:
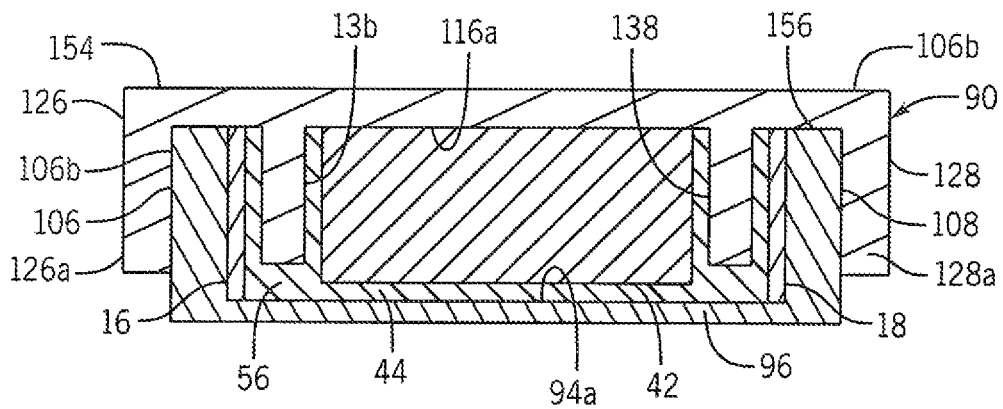
FIG. 11 is a cross-sectional view of the top and bottom portion of the mold in an assembled configuration housing the base of the stamp of the present invention.

Stamp 10 may be fabricated from a mold, generally designated by the reference numeral 90, FIG. 11. Mold 90 includes lower portion 92, FIG. 9b, and upper portion 94, FIG. 9a. Referring to FIG. 9b, lower portion 92 has a box-like configuration and is defined by lower wall 96 having first and second sidewalls 98 and 100, respectively, projecting from opposite sides 102 and 104 of lower wall 96 and first and second end walls 106 and 108, respectively, projecting from opposite ends 110 and 112 of lower wall 96. Inner surfaces 98a and 100a of first and second sidewalls 98 and 100, respectively, and inner surfaces 106a and 108a of first and second end walls 106 and 108, respectively, define mold cavity 114. Mold cavity 114 is adapted for receiving base 11 therein, FIG. 10, for reasons hereinafter described.

Referring back to FIG. 9a, upper portion 94 of mold 90 also has a box-like configuration and is defined by upper wall 116 having first and second sidewalls 118 and 120, respectively, projecting from opposite sides 122 and 124 of upper wall 116 and first and second end walls 126 and 128, respectively, projecting from opposite ends 130 and 132 of upper wall 116. Inner surfaces 118a and 120a of first and second sidewalls 118 and 120, respectively, and inner surfaces 126a and 128a of first and second end walls 126 and 128, respectively, define lower portion receipt cavity 134. Lower portion receipt cavity 134 is adapted for receiving lower portion 92 of mold 90 therein, FIG. 11, as hereinafter described. First and second well forming projections 136 and 138, respectively, extending from inner surface 116a of upper wall 116 into lower portion receipt cavity 134. First and second well forming projections 136 and 138, respectively, correspond in size, shape and location to first well 56 formed in upper surface 54 of first portion 52 of gel 50 and second well 62 formed in upper surface 56 of second portion 58 of gel 50, respectively.

In order to fabricate stamp 10, base 11 is positioned in mold cavity 114 such that lower edges 12b and 14b of first and second side walls 12 and 14, respectively, and lower edges 16b and 18b of first and second end walls 16 and 18, respectively, engage upper surface 96a of lower wall 96, FIG. 10. Inner surfaces 98a and 100a of first and second sidewalls 98 and 100, respectively, and inner surfaces 106a and 108a of first and second end walls 106 and 108, respectively, abut corresponding outer surfaces 142 and 144 of first and second side walls 12 and 14, respectively, and outer surfaces 146 and 148 first and second end walls 16 and 18, respectively, with base 11 received in mold cavity 114 so as to prevent lateral movement of base 11 during the molding process. With base 11 receiving in mold cavity 114, upper surface 22 of central portion 20 of base 11, upper edges 12a and 14a of first and second side walls 12 and 14, respectively, and upper edges 16a and 16b of first and second end walls 16 and 18, respectively, and generally co-planar with upper edges 150 and 152 of first and second sidewalls 98 and 100, respectively, and upper edges 154 and 156 of first and second end walls 106 and 108, respectively.

After inserting base 11 into mold cavity 114, upper portion 94 of mold 90 is positioned on lower portion 92, FIG. 11. More specifically, lower portion 92 is inserted into lower portion receipt cavity 134 such that upper edges 150 and 152 of first and second sidewalls 98 and 100, respectively, and upper edges 154 and 156 of first and second end walls 106 and 108, respectively, engage inner surface 116a of upper wall 116 of upper portion 94. First and second well forming projections 136 and 138, respectively, extend into first and second gel cavities 36 and 40, respectively. Inner surfaces 118a and 120a of first and second sidewalls 118 and 120, respectively, and inner surfaces 126a and 128a of first and second end walls 126 and 128, respectively, of upper portion 94 abut corresponding outer surfaces 98b and 100b of first and second sidewalls 98 and 100, respectively, and outer surfaces 106b and 108b of first and second end walls 106 and 108, respectively, of lower portion 92 so as to prevent lateral movement of lower portion 92 during the molding process.

Figure 12:
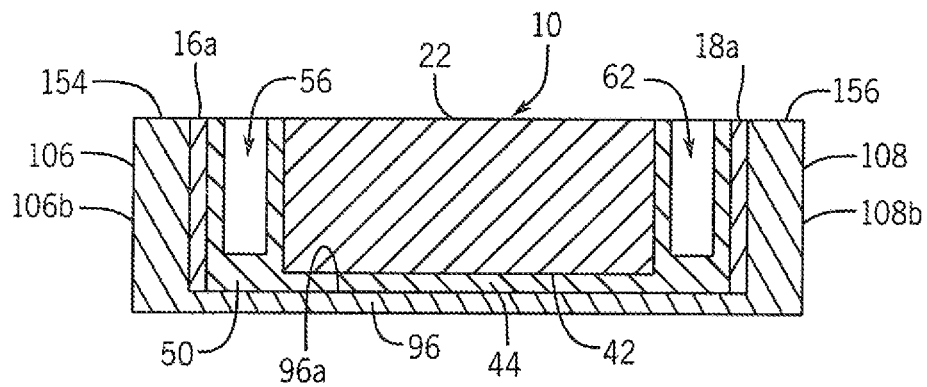
FIG. 12 is a cross-sectional view of the stamp of the present invention within the bottom portion of the mold after the fabrication thereof.

With lower portion 92 received with lower portion receipt cavity portion 134 of upper portion, gel 50 is inserted into mold 90 so as to be received in first and second gel cavities 36 and 40, respectively, and in gradient cavity 44 along lower surface 42 of central portion 20 of base 11. As previously noted, first and second well forming projections 136 and 138, respectively, prevent gel 50 from occupying the portions of first and second gel cavities 36 and 40, respectively, corresponding to first well 56 and second well 62, respectively. Thereafter, gel 50 is polymerized within first and second gel cavities 36 and 40, respectively, and gradient cavity 44. Mold 90 may then be disassembled so as to allow stamp 10 to be removed therefrom. It is contemplated to initially remove upper portion 94 of mold 90 from lower portion 92 of mold 90, FIG. 12. With stamp 10 positioned within mold cavity 114 of lower portion 92 of mold 90, a user may introduce the concentration of gradient particles in third portion 64 of gel 50, as heretofore described. As a result, when removed from mold cavity 114 of lower portion 92 of mold 90, stamp 10 would be ready for immediate use on a cell culture, as heretofore described.

Figure 13:
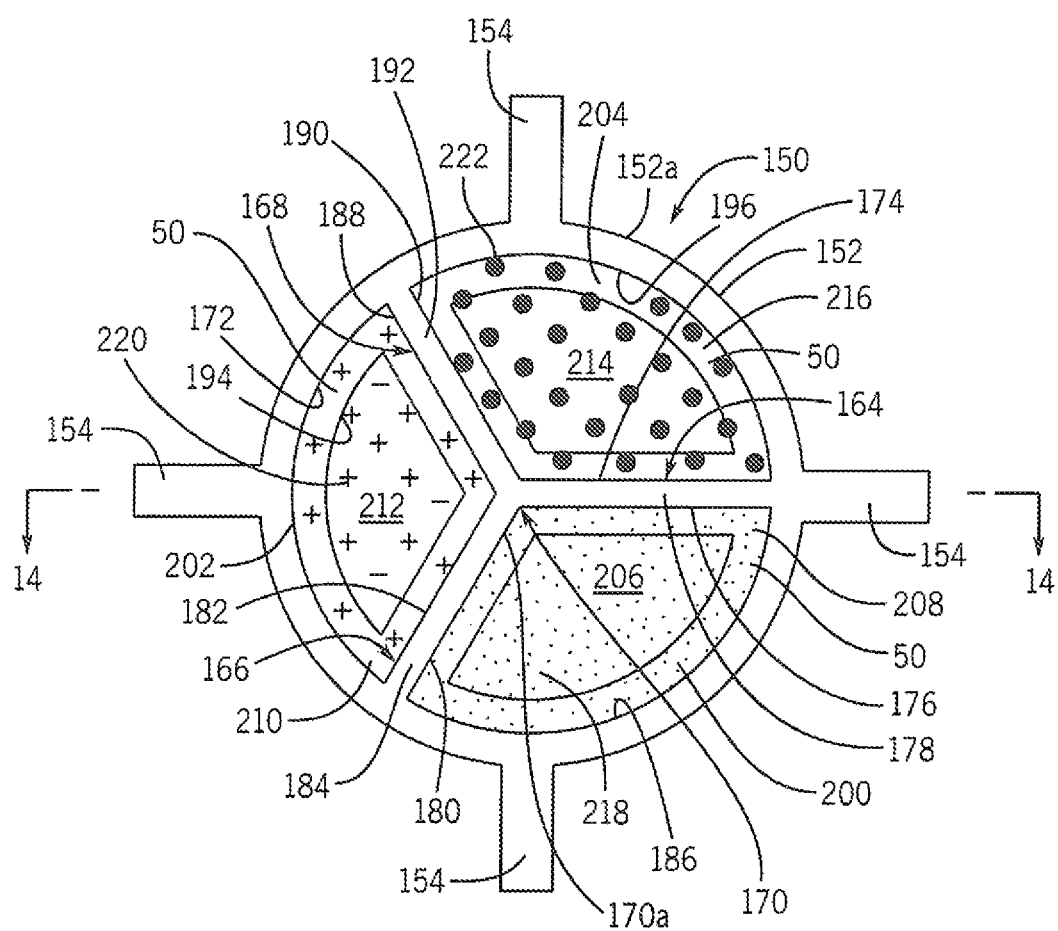
FIG. 13 is a top plan view of an alternate embodiment of a stamp in accordance with the present invention.
Figure 14:
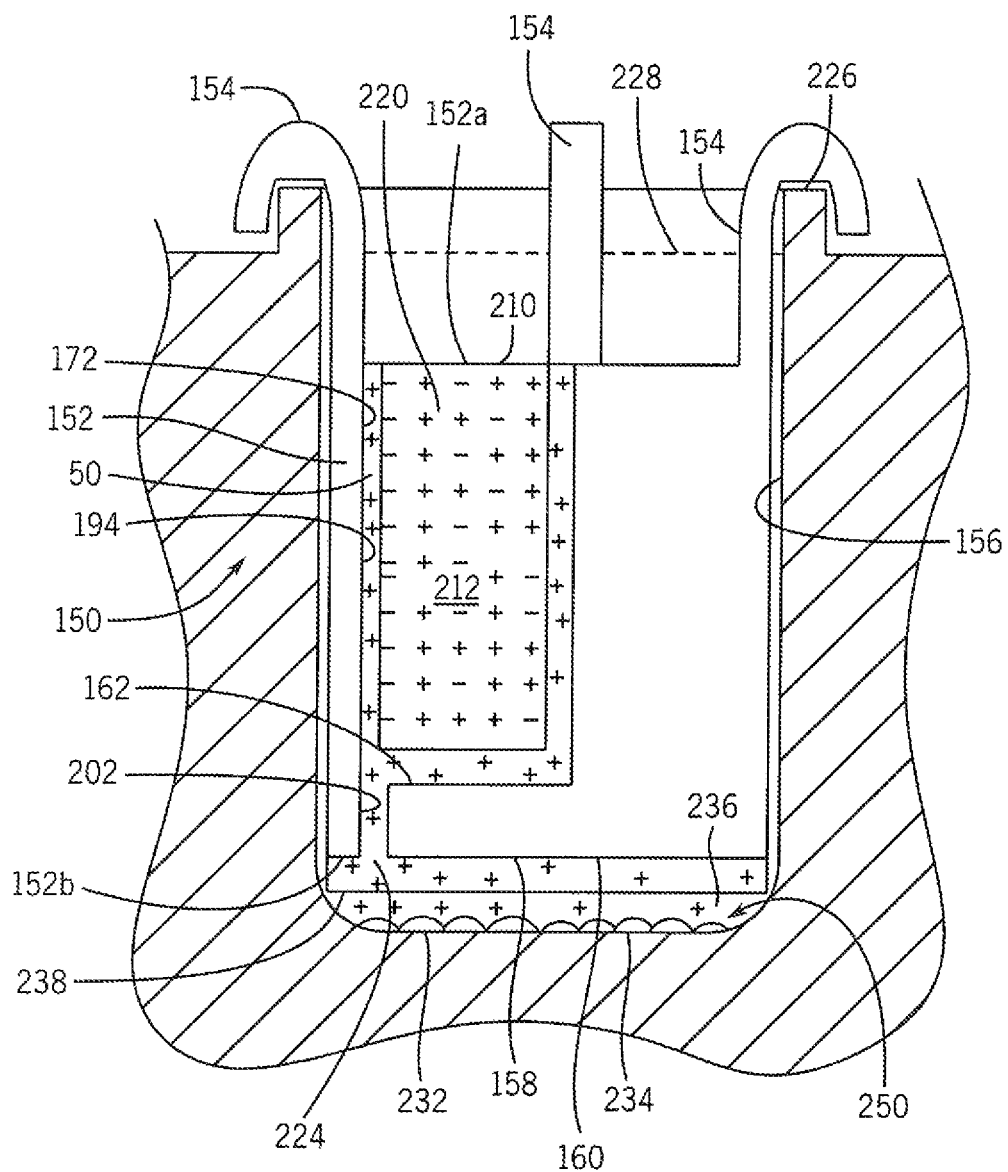
FIG. 14 is a cross sectional view of the stamp of the present invention taken along line 14-14 of FIG. 13.

It is contemplated to modify stamp 10 to provide additional concentration gradients of various particles (e.g. 3 different particles) in gel 50. Referring to FIGS. 13-14, an alternate embodiment of a stamp in accordance with the present invention is generally designated by the reference numeral 150. Stamp 150 has a generally circular configuration, FIG. 13, and is defined by a circular sidewall 152 having an upper edge 152a and a lower edge 152b. A plurality of circumferentially spaced hooks 154 extend from upper edge 152a and are adapted from supporting stamp 150 in a well 156, as hereinafter described. Stamp 150 further includes bottom wall 158 having a lower surface 160 being generally coplanar with lower edge 152b of sidewall 152 and an upper surface 162.

Stamp 150 further includes first, second and third partitions 164, 166 and 168 extending radially outward from and circumferentially spaced about central hub 170. Central hub 170 extends from upper surface 162 of bottom wall 158 and terminates at upper edge 170a which is coplanar with upper edge 152a of sidewall 152. First partition 164 extends from upper surface 162 of bottom wall 158 between central hub 170 and inner surface 172 of sidewall 152. First partition 164 is defined by first and second sides 174 and 176, respectively, and upper edge 178 which is coplanar with upper edge 152a of sidewall 152 and upper edge 170a of central hub 170. Second partition 166 extends from upper surface 162 of bottom wall 158 between central hub 170 and inner surface 172 of sidewall 152. Second partition 166 is defined by first and second sides 180 and 182, respectively, and upper edge 184 which is coplanar with upper edge 152a of sidewall 152 and upper edge 170a of central hub 170. First side 180 of second partition 166 and second side 176 of first partition 164 define first gel cavity 186 therebetween. Third partition 168 extends from upper surface 162 of bottom wall 158 between central hub 170 and inner surface 172 of sidewall 152. Third partition 168 is defined by first and second sides 188 and 190, respectively, and upper edge 192 which is coplanar with upper edge 152a of sidewall 152 and upper edge 170a of central hub 170. First side 188 of third partition 168 and second side 182 of second partition 166 define second gel cavity 194 therebetween. First side 174 of first partition 164 and second side 190 of third partition 168 define third gel cavity 196 therebetween. First, second and third passages 200, 202 and 204 extend through bottom wall 158 of stamp 110 and communicate with corresponding first, second and third gel cavities 186, 194 and 196, respectively.

Gel 50 is provided in first, second and third gel cavities 186, 194 and 196, respectively, and first, second and third passages 200, 202 and 204, respectively. In addition, gel 50 is provided along lower surface 160 of bottom wall 158. As heretofore described, it is contemplated for gel 50 to take the form of an agarose gel. As is known, agarose gel has a high degree of physical, chemical and thermal stability and exhibits limited interaction with biomolecules. It is noted, however, the gel 50 may take other forms without deviating from the scope of the present invention.

Gel 50 in first gel cavity 186 defines first gel well 206 formed the upper surface 208 thereof. In the depicted embodiment, first gel well 206 has a generally pie-shaped cross section. However, other configurations of first gel well 206 are possible without deviating from the scope of the present invention. Gel 50 in second gel cavity 194 defines second gel well 212 formed in upper surface 210 thereof. In the depicted embodiment, second gel well 212 has a generally pie-shaped cross section. However, other configurations of second gel well 212 are possible without deviating from the scope of the present invention. Gel 50 in third gel cavity 196 defines third gel well 214 formed in upper surface 216 thereof. In the depicted embodiment, third gel well 214 has a generally pie-shaped cross section. However, other configurations of third gel well 214 are possible without deviating from the scope of the present invention.

In operation, first, second and third gel wells 206, 212 and 214, respectively, are filled with corresponding predetermined fluids, having a known concentration of particles 218, 220 and 222, respectively, therein, such as cells, molecules, chemical species, organisms or the like. Molecules may include those that influence cell behaviors, such as chemokines that induce chemotactic migration, morphogens that influence differentiation and development, or growth factors that stimulate proliferation. Chemical species such as cell function inhibitors/activators or nutrients may also be patterned. Alternatively, cell-sourced molecules may be patterned by culturing mammalian or microbial cells in one or more gel cavities. Thereafter, the predetermined fluids diffuse through gel 50 in first, second and third gel cavities 186, 194 and 196, respectively, and through first, second and third passages 200, 202 and 204, respectively, in bottom wall 158 into portion 224 of gel 50 provided along lower surface 160 of bottom wall 158 so as to create three concentration gradients of particles in portion 224 of gel 50 provided along lower surface 160 of bottom wall 158 over a predetermined time period.

Referring to FIG. 14, during or after the gradients have formed in portion 224 of gel 50 provided along lower surface 160 of bottom wall 158, stamp 150 is inserted into well 156 such that hooks 154 engage support wall 226 extending about opening 228 of well 156. With stamp 150 received in well 156, portion 224 of gel 50 provided along lower surface 160 of bottom wall 158 is positioned over a cell culture, generally designated by the reference numeral 230, which has been provided on cell culture surface 232 at the bottom of well 156. Cell culture 230 includes a plurality of cells 234 received within cell culture media 236. Stamp 150 is positioned such that lower surface 238 of portion 224 of gel 50 provided along lower surface 160 of bottom wall 158 communicates with cell culture media 236. Stamp 150 in maintained in positioned for a desired incubation period. During the incubation period, particles 218, 220 and 222 in gel 50 diffuse from lower surface 238, through cell culture media 236 and into the plurality of cells 234 to provide for gradient registered cells. At the conclusion of the incubation period, stamp 150 is removed and the gradient registered cells are processed according to a desired application, as heretofore described.

Various modes of carrying out the invention are contemplated as being within the scope of the following claims particularly pointing out and distinctly claiming the subject matter, which is regarded as the invention.

We claim:

1. A method of transmitting particles to cells of a cell culture, comprising the steps of:
    providing the cell culture on a surface;
    patterning the particles in a gel extending along a portion of a lower surface of a stamp;
    positioning the stamp with the particles patterned in the gel such that the particles in the gel extending along the lower surface of the stamp communicate with the cells of the cell culture; and
    allowing the particles in the gel to diffuse into the cells of the cell culture.

2. The method of claim 1 wherein the stamp includes:
    a body having an upper surface, a lower surface having a recessed portion, and first and second passages extending between the upper surface and the recessed portion of lower surface thereof;
    wherein the gel extends along the recessed portion of the lower surface of the body.

3. The method of claim 2 wherein the body includes the first and second passages extending between the upper surface and the recessed portion of lower surface thereof, the gel being received in the first and second passages through the body.

4. The method of claim 3 wherein:
    the gel in the first passage defining a first well, the first well being adapted for receiving a first solution therein; and
    the gel in the second passage defines a second well, the second well being adapted for receiving a second solution therein.

5. The method of claim 1 wherein the step of patterning the particles includes the additional steps of:
    depositing a first solution in the first well, the first solution including the particles; and
    allowing the particles to diffuse into the gel.

6. The method of claim 5 wherein the particles in the gel form a gradient between the first and second passages in the body along the recessed portion of the lower surface.

7. The method of claim 1 comprising the additional step of depositing cell culture media on the cell culture prior to the step of positioning the stamp.

8. A method of transmitting particles to cells of a cell culture, comprising the steps of:
    forming a cell culture on a base;
    patterning the particles in a gel extending along a lower surface of a stamp;
    depositing cell culture media on the cell culture;
    positioning the stamp with the particles patterned in the gel in the cell culture media such that the particles in the gel extending along the lower surface of the stamp communicate with the cells of the cell culture; and
    allowing the particles in the gel to diffuse into the cells of the cell culture through the cell culture media.

9. The method of claim 8 wherein the stamp includes:
    a body having an upper surface, a lower surface having a recessed portion, and first and second passages extending between the upper surface and the recessed portion of lower surface thereof;
    wherein the gel extends along the recessed portion of the lower surface of the body.

10. The method of claim 9 wherein the body includes the first and second passages extending between the upper surface and the recessed portion of lower surface thereof, the gel being received in the first and second passages through the body.

11. The method of claim 10 wherein:
    the gel in the first passage defining a first well, the first well being adapted for receiving a first solution therein; and
    the gel in the second passage defines a second well, the second well being adapted for receiving a second solution therein.

12. The method of claim 8 wherein the step of patterning the particles includes the additional steps of:
    depositing a first solution in a first well, the first solution including the particles; and
    allowing the particles to diffuse into the gel.

13. The method of claim 12 wherein the particles in the gel form a gradient between the first and second passages in the body along the recessed portion of the lower surface.

14. The method of claim 13 wherein the particles are first particles and wherein the method further comprises the additional steps of:
    depositing a second solution in the second well, the second solution including second particles; and
    allowing the second particles to diffuse into the gel.

15. The method of claim 14 wherein the second particles in the gel form a second gradient from the second well to the first well along the recessed portion of the lower surface.

* * * * *